(12) United States Patent
Mita et al.

(10) Patent No.: US 9,080,995 B2
(45) Date of Patent: Jul. 14, 2015

(54) METHOD FOR QUANTITATIVELY ANALYZING CYSTEINE AND CYSTINE AND REAGENT KIT FOR QUANTITATIVELY ANALYZING CYSTEINE AND CYSTINE

(71) Applicants: SHISEIDO COMPANY, LTD., Tokyo (JP); KYUSHU UNIVERSITY, NATIONAL UNIVERSITY CORPORATION, Fukuoka (JP)

(72) Inventors: Masashi Mita, Tokyo (JP); Kenji Hamase, Fukuoka (JP)

(73) Assignees: SHISEIDO COMPANY, LTD., Tokyo (JP); Kyusyu University, National University Corporation, Fukuoka (JP)

( * ) Notice: Subject to any disclaimer, the term of this patent is extended or adjusted under 35 U.S.C. 154(b) by 0 days.

(21) Appl. No.: 14/472,982

(22) Filed: Aug. 29, 2014

(65) Prior Publication Data
US 2015/0064797 A1 Mar. 5, 2015

(51) Int. Cl.
*G01N 33/68* (2006.01)
*G01N 31/00* (2006.01)

(52) U.S. Cl.
CPC .......... *G01N 31/005* (2013.01); *G01N 33/6815* (2013.01); *Y10T 436/182* (2015.01)

(58) Field of Classification Search
CPC . G01N 31/005; G01N 33/68; G01N 33/6806; G01N 33/6809; G01N 33/6812; G01N 33/6815; G01N 30/02; G01N 30/04; Y10T 436/173845; Y10T 436/18; Y10T 436/182; Y10T 436/20; Y10T 436/201666; Y10T 436/24
USPC ............... 436/86, 89, 90, 106, 111, 119, 120, 436/127, 129, 161, 164, 172, 173; 422/68.1, 70, 82.05, 82.08, 430
See application file for complete search history.

(56) References Cited

U.S. PATENT DOCUMENTS

| | | | | |
|---|---|---|---|---|
| 6,902,936 B2* | 6/2005 | Qiu et al. | ......... | 436/86 |
| 2002/0102744 A1* | 8/2002 | Snyder et al. | ......... | 436/538 |
| 2005/0276727 A1* | 12/2005 | Pawliszyn et al. | ......... | 422/99 |
| 2007/0218561 A1* | 9/2007 | Goldman | ......... | 436/89 |
| 2011/0217707 A1* | 9/2011 | Hamase et al. | ......... | 435/6.11 |

* cited by examiner

*Primary Examiner* — Maureen Wallenhorst
(74) *Attorney, Agent, or Firm* — IPUSA, PLLC

(57) ABSTRACT

A method for quantitatively analyzing cysteine and cysteine includes a first step of adding a methyl-sulfurating agent to a sample that includes cysteine and cystine to obtain a methyl-sulfurated cysteine, a second step of adding a derivatizing agent to the methyl-sulfurated cysteine and the cystine to obtain a cysteine derivative and a cystine derivative, respectively, and a third step of quantifying the cysteine derivative and the cystine derivative.

9 Claims, 3 Drawing Sheets

METHOD FOR QUANTITATIVELY ANALYZING CYSTEINE AND CYSTINE AND REAGENT KIT FOR QUANTITATIVELY ANALYZING CYSTEINE AND CYSTINE

BACKGROUND OF THE INVENTION

1. Field of the Invention

An aspect of the present invention relates to at least one of a method for quantitatively analyzing cysteine and cystine and a reagent kit for quantitatively analyzing cysteine and cystine.

2. Description of the Related Art

Methionine, cysteine, and cystine are known as sulfur-containing amino acids that constitute a protein in a living body. These maintain homeostasis through a successive metabolic cycle in a living body. For example, methionine is usually metabolized to cysteine in a living body, and homocysteine produced as an intermediate in this metabolic process is derived into cysteine after formation of cystathionine due to condensation with serine.

Among these, attention is paid to cysteine as a candidate of an index for understanding a cause of metabolic disorder of a sulfur-containing amino acid or an oxidation-reduction-associated disease, and a measurement of a concentration thereof in a living body, for example, in blood is important.

However, because cysteine has a thiol group, this thiol group is oxidized to produce cystine through an oxidation-reduction reaction of a system where cysteine is present. Accordingly, it is difficult to quantify a content of each of cysteine and cystine in a living body accurately.

SUMMARY OF THE INVENTION

According to one aspect of the present invention, there is provided a method for quantitatively analyzing cysteine and cystine, including a first step of adding a methyl-sulfurating agent to a sample that includes cysteine and cystine to obtain a methyl-sulfurated cysteine, a second step of adding a derivatizing agent to the methyl-sulfurated cysteine and the cystine to obtain a cysteine derivative and a cystine derivative, respectively, and a third step of quantifying the cysteine derivative and the cystine derivative.

According to another aspect of the present invention, there is provided a reagent kit for quantitatively analyzing cysteine and cystine, including a methyl-sulfurating agent configured to methyl-sulfurate cysteine to obtain a methyl-sulfurated cysteine, and a derivatizing agent configured to derivatize the methyl-sulfurated cysteine and cystine to obtain a cysteine derivative and a cystine derivative, respectively.

DETAILED DESCRIPTION OF THE PREFERRED EMBODIMENTS

An embodiment of the present invention will be described below.

The inventors have found that, in analysis of cysteine and cystine, for example, by using a column chromatography method, more preferably, by utilizing a high-performance liquid chromatography (HPLC) method, cysteine is methyl-sulfurated by using a methyl-sulfurizing agent, and an obtained S-(methylthio)cysteine and cystine are derivatized by using a derivatizing agent to be provided for analysis, so that it is possible to analyze each of cysteine and cystine quantitatively. Furthermore, it has been found that it is also possible to conduct optical resolution of cysteine and cystine in this analysis and it is possible for a quantification method according to the present embodiment to conduct quantitative analysis of each of L-cysteine, D-cysteine, L-cystine, and D-cystine.

(A Quantification Method)

Figure 1:
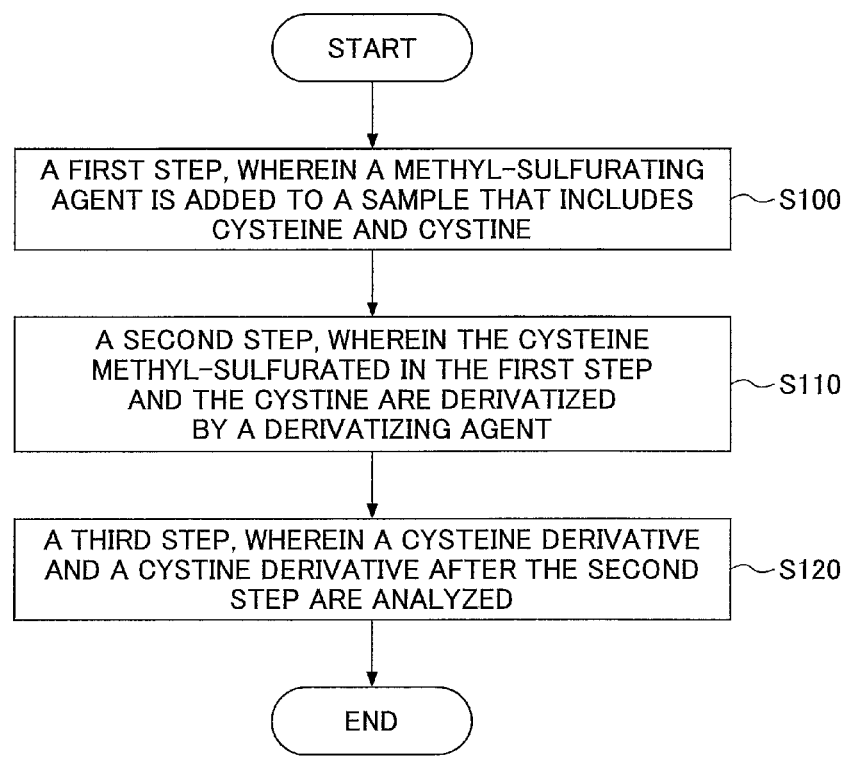
FIG. 1 is a flow diagram of one example of a quantification method according to the present embodiment.

Next, a method of quantification of cysteine and cystine according to the present embodiment will be described in detail. FIG. 1 illustrates a flow diagram of one example of a quantification method according to the present embodiment.

A quantification method according to the present embodiment has a first step (S100) wherein a methyl-sulfurating agent is added to a sample that includes cysteine and cystine, a second step (S110) wherein the cysteine that has been methyl-sulfurated in the first step and the cystine are derivatized by a derivatizing agent, and a third step (S120) wherein a cysteine derivative and a cystine derivative after the second step are analyzed.

Each of the steps will be described in detail below.

Figure 2:
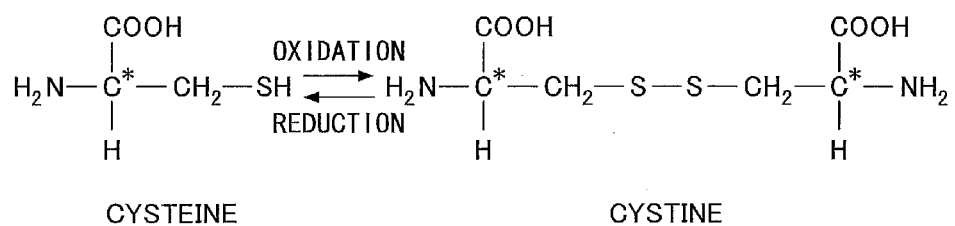
FIG. 2 is a schematic diagram for illustrating an equilibrium state between cysteine and cystine.

A schematic diagram for illustrating an equilibrium state between cysteine and cystine is illustrated in FIG. 2. Two cysteine molecules are oxidized to bond thiol groups thereof mutually and produce cystine. Furthermore, cystine is reduced to be changed into cysteine. That is, a change in a content of each of cysteine and cystine in a system is caused depending on a oxidation-reduction state. Because a state in vitro is at a high oxygen potential as compared to that in vivo, it has been difficult to know contents of cysteine and cystine in vivo accurately.

However, a quantification method according to the present embodiment has a first step of S100 wherein a methyl-sulfurating agent is added to a sample that includes cysteine and cystine. Herein, for a methyl-sulfurating agent, it is possible to use, for example, methanethiosulfonic acid S-methyl ester (MMTS, below).

Figure 3:
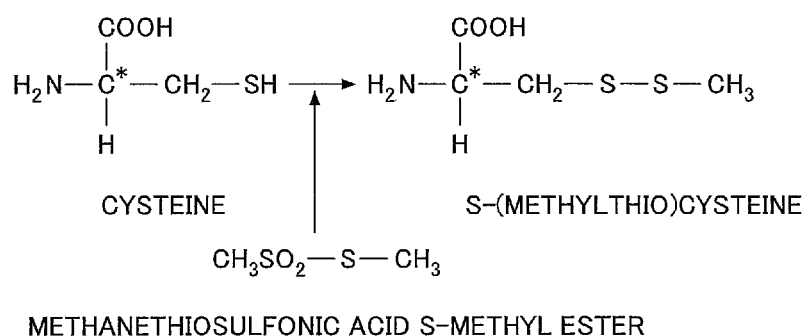
FIG. 3 is a schematic diagram for illustrating methyl-sulfuration of cysteine.

A schematic diagram for illustrating methyl-sulfuration of cysteine is illustrated in FIG. 3.

As illustrated in FIG. 3, at a first step, cysteine is alkylated immediately, specifically, during about several seconds, to produce S-(methylthio)cysteine. Furthermore, because a thiol group in a molecule thereof is blocked due to this reaction, production of cystine due to a change in an oxidation-reduction potential is stopped.

Next, at a second step of S110, S-(methylthio)cysteine and cystine are derivatized by a derivatizing agent. In the present embodiment, 4-fluoro-7-nitro-2,1,3-benzoxadiazole (NBD-F, below) is used as a derivatizing agent.

NBD-F has been known as a derivatizing reagent for HPLC that is generally used for fluorescent derivatization of a primary or secondary amine, an amino acid, or the like. It is preferably used because it is possible to derivatize an amino acid on a mild condition and further a stability of a reagent after derivatization is high so that a sensitivity of a sample is not degraded due to a temporal change.

Then, an amino acid derivative that has been derivatized by NBD-F is subjected to HPLC analysis at a next third step, so that it is possible to quantify a content of each of cysteine and cystine in an original sample.

In the present embodiment, separation is conducted by using a two-dimensional liquid chromatography device wherein a reversed-phase column and an optical resolution column are coupled, and detection is conducted by a fluorescence detector or a mass spectrometer so that analysis is conducted.

Next, an embodiment of the present invention will be described in more detail by describing specific embodiments.

A First Embodiment

An embodiment will be described for confirming that it is possible for a quantification method according to the present embodiment to quantify a content of each of cysteine and cystine accurately.

15 μL of a 400 mM boric acid buffer solution (pH=8.0) were added to 10 μL of a 100 mM hydrochloric acid solution that contained cysteine and cystine and further 5 μL of an MMTS solution with a concentration of 1.5 mM (solvent: acetonitrile) were added thereto. An obtained solution was stood at 25° C. for 10 minutes to methyl-sulfurating cysteine.

Then, 5 μL of an NBD-F solution with a concentration of 40 mM (solvent: acetonitrile) were added to this solution, and heating thereof was conducted at 60° C. for 2 minutes to fluorescent-derivatize S-(methylthio)cysteine and cystine.

After 50 μL of a 2% aqueous solution of trifluoroacetic acid were added to stop a reaction, 415 μL of a purified water were added thereto and 5 μL of a reaction solution were directly injected into an HPLC device. Here, a separated sample was detected by a fluorescence detector. Measurement wavelengths of the fluorescence detector were an excitation wavelength of 470 nm and a fluorescence wavelength of 530 nm.

Furthermore, a sample as a comparative embodiment was prepared by a similar method except that MMS was not added, and was subjected to HPLC analysis.

Analysis conditions for HPLC analysis were:
for reversed-phase separation,
a column: monolithic ODS column (0.53 mm i.d.×1000 mm);
a flow rate: 25 μL/min;
a temperature: 45° C.; and
a mobile phase: an aqueous solution that contained acetonitrile and trifluoroacetic acid; and
for optical resolution,
a column: Sumichiral OA-2500S (1.5 mm i.d.×250 mm);
a flow rate: 200 μL/min;
a temperature: 25° C.; and
a mobile phase: a mixed solution of methanol and acetonitrile that contained formic acid.

Figure 4:
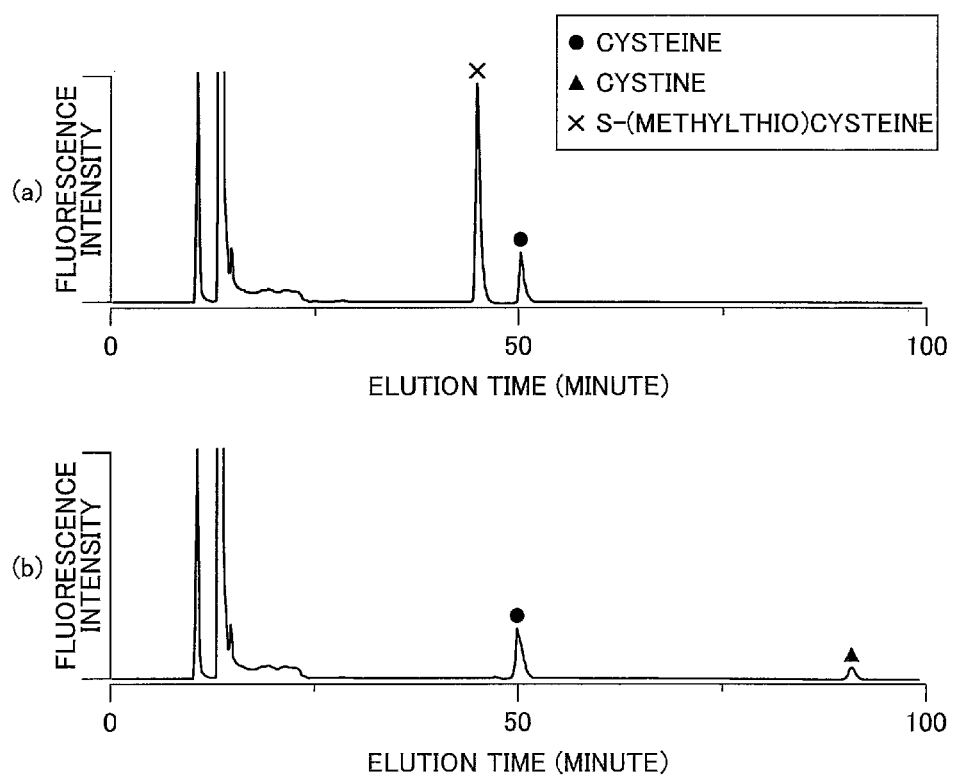
FIG. 4 is one example of a result of HPLC/FL analysis for reversed-phase separation.

FIG. 4 illustrates one example of a result of HPLC/FL analysis for reversed-phase separation. In FIG. 4, a transverse axis is for an elution time and a longitudinal axis is for an fluorescence intensity. Furthermore, FIG. 4($a$) is one example of a result of a case where MMTS according to the present embodiment was added and FIG. 4($b$) is one example of a result of a case where MMTS was not added.

In regard to an equilibrium state between cysteine and cystine, such an equilibrium at a general oxidation-reduction potential in vitro is shifted in such a manner that cystine is produced and peak intensities of cysteine and cystine as illustrated in FIG. 4($b$) are changed.

However, cysteine in a quantification method according to the present embodiment is preliminarily changed into S-(methylthio)cysteine because MMTS is added thereto. Accordingly, it is possible to conduct a measurement in such a manner that peaks of fluorescence originating from S-(methylthio)cysteine and cystine reflect a state in vitro without being influenced by post-sampling one.

Figure 5:
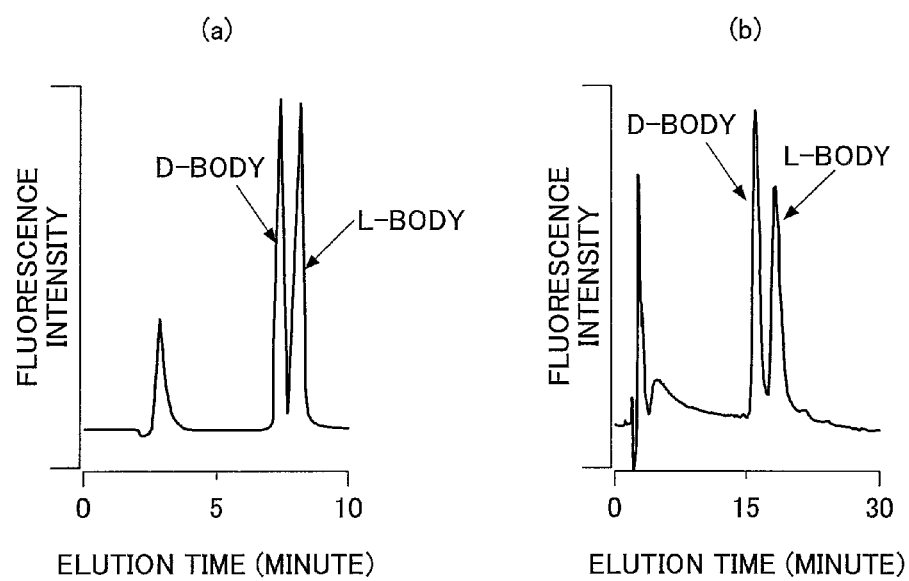
FIG. 5 is one example of a result of HPLC/FL analysis for optical resolution.

FIG. 5 illustrates one example of a result of HPLC/FL analysis for optical resolution. FIG. 5 ($a$) is a result for S-(methylthio)cysteine and FIG. 5 ($b$) is a result for cystine. In FIG. 5, a transverse axis is for an elution time and a longitudinal axis is for a fluorescence intensity.

As illustrated in FIG. 5 ($a$) and FIG. 5 ($b$), it is possible for a quantification method according to the present embodiment to optically distinguish between and quantify a D-body and an L-body with respect to peaks originating from S-(methylthio)cysteine and cystine. That is, it was found that a quantification method according to the present embodiment was a method that was capable of distinguishing between a D-body and an L-body and accurately quantifying a content of each of cysteine and cystine.

A Second Embodiment

Next, an embodiment will be described for confirming that it is also possible to implement a quantification method according to the present embodiment by a detection method other than fluorescence detection.

Quantification was conducted by a method similar to that of the first embodiment except that a sample separated by an HPLC device was detected by a tandem-type mass spectrometer. For mass spectrometry, mass spectrometry was conducted for a product ion with a mass-to-charge ratio (M/Z) of 283 that was produced from a precursor ion with an M/Z of 331.

Figure 6:
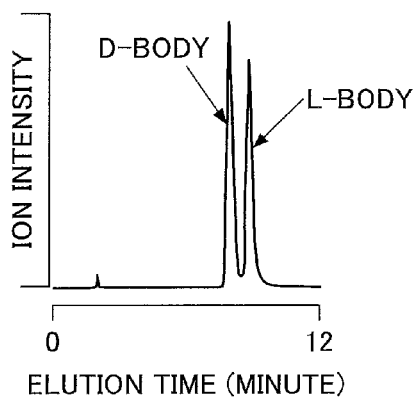
FIG. 6 is one example of a result of HPLC/MS analysis for optical resolution.

FIG. 6 illustrates one example of a result of HPLC/MS analysis for optical resolution. FIG. 6 is a result for S-(methylthio)cysteine, wherein a transverse axis is for an elution time and a longitudinal axis is for an ion intensity.

As illustrated in FIG. 6, it was found that a quantification method according to the present embodiment was a method that was also capable of distinguishing between a D-body and an L-body and accurately quantifying a content of each of cysteine and cystine by a detection method with a mass spectrometer.

APPENDIX

An Illustrative Embodiment(s) of a Quantification Method and a Quantification Reagent Kit for Cysteine and Cystine At least one illustrative embodiment of the present invention may relate to a quantification method and a quantification reagent kit for cysteine and cystine.

At least one illustrative embodiment of the present invention may aim at providing a quantification method that is capable of quantifying a content of each of cysteine and cystine accurately, against a problem as described above.

At least one illustrative embodiment of the present invention may be provided as a quantification method for cysteine and cysteine, that has a first step of adding a methyl-sulfurating agent to a sample that includes cysteine and cystine, a second step of derivatizing the cysteine methyl-sulfurated in the first step and the cystine by a derivatizing agent, and a third step of analyzing a cysteine derivative and a cystine derivative after the second step.

Illustrative embodiment (1) is a quantification method for cysteine and cystine, that has a first step of adding a methyl-sulfurating agent to a sample that includes cysteine and cystine, a second step of derivatizing the cysteine methyl-sulfurated in the first step and the cystine by a derivatizing agent, and a third step of analyzing a cysteine derivative and a cystine derivative after the second step.

Illustrative embodiment (2) is the quantification method as described in illustrative embodiment (1), wherein the third step analyzes a cysteine derivative and a cystine derivative after the second step by distinguishing optical isomers.

Illustrative embodiment (3) is the quantification method as described in illustrative embodiment (1) or (2), wherein the methyl-sulfurating agent includes methanethiosulfonic acid S-methyl ester.

Illustrative embodiment (4) is the quantification method as described in any one of illustrative embodiments (1) to (3), wherein the derivatizing agent includes 4-fluoro-7-nitro-2,1,3-benzoxadiazole.

Illustrative embodiment (5) is the quantification method as described in any one of illustrative embodiments (1) to (4), wherein the third step includes a step of detecting each of the derivatives by using a fluorescence detection liquid chromatograph device.

Illustrative embodiment (6) is the quantification method as described in any one of illustrative embodiments (1) to (4), wherein the third step includes a step of detecting each of the derivatives by using a liquid chromatograph/mass spectrometric device.

Illustrative embodiment (7) is a quantification reagent kit for quantifying at least one of cysteine and cystine in a sample that includes cysteine and cystine, that includes a methyl-sulfurating agent and a fluorescent derivatizing agent.

Illustrative embodiment (8) is the quantification reagent kit as described in illustrative embodiment (7), wherein the methyl-sulfurating agent includes methanethiosulfonic acid S-methyl ester.

Illustrative embodiment (9) is the quantification reagent kit as described in illustrative embodiment (7) or (8), wherein the derivatizing agent includes 4-fluoro-7-nitro-2,1,3-benzoxadiazole.

According to at least one illustrative embodiment of the present invention, it may be possible to provide a quantification method that is capable of quantifying a content of each of cysteine and cystine accurately.

Although the illustrative embodiment(s) and specific example(s) of the present invention have been described with reference to the accompanying drawings, the present invention is not limited to any of the illustrative embodiment(s) and specific example(s) and the illustrative embodiment(s) and specific example(s) may be altered, modified, or combined without departing from the scope of the present invention.

What is claimed is:

1. A method for quantitatively analyzing cysteine and cystine, comprising:
    a first step of adding a methyl-sulfurating agent to a sample that includes cysteine and cystine to obtain a methyl-sulfurated cysteine;
    a second step of adding a derivatizing agent to the methyl-sulfurated cysteine and the cystine to obtain a cysteine derivative and a cystine derivative, respectively; and
    a third step of quantifying the cysteine derivative and the cystine derivative.

2. The method as claimed in claim 1, wherein the third step includes distinguishing between optical isomers of the cysteine derivative and the cystine derivative.

3. The method as claimed in claim 1, wherein the methyl-sulfurating agent includes methanethiosulfonic acid S-methyl ester.

4. The method as claimed in claim 1, wherein the derivatizing agent includes 4-fluoro-7-nitro-2,1,3-benzoxadiazole.

5. The method as claimed in claim 1, wherein the third step includes detecting the cysteine derivative and the cystine derivative by using a fluorescence detection liquid chromatograph device.

6. The method as claimed in claim 1, wherein the third step includes detecting the cysteine derivative and the cystine derivative by using a liquid chromatograph-mass spectrometric device.

7. A reagent kit for quantitatively analyzing cysteine and cystine, comprising:
    a methyl-sulfurating agent configured to methyl-sulfurate cysteine to obtain a methyl-sulfurated cysteine; and
    a derivatizing agent configured to derivatize the methyl-sulfurated cysteine and cystine to obtain a cysteine derivative and a cystine derivative, respectively.

8. The reagent kit as claimed in claim 7, wherein the methyl-sulfurating agent includes methanethiosulfonic acid S-methyl ester.

9. The reagent kit as claimed in claim 7, wherein the derivatizing agent includes 4-fluoro-7-nitro-2,1,3-benzoxadizaole.

* * * * *